United States Patent [19]
Takahashi et al.

[11] Patent Number: 5,741,461
[45] Date of Patent: Apr. 21, 1998

[54] AUTOMATIC ANALYZER HAVING CUVETTE CLEANING CONTROL DEVICE

[75] Inventors: Kenichi Takahashi, Hitachinaki; Tomonori Mimura, Tomobe-machi; Naoto Oki, Hitachinaka; Kyoko Imai, Hitachinaka; Isao Shindo, Hitachinaka; Kahei Shiraishi, Hitachioota, all of Japan

[73] Assignee: Hitachi, Ltd., Tokyo, Japan

[21] Appl. No.: 645,075

[22] Filed: May 13, 1996

[30] Foreign Application Priority Data

May 19, 1995 [JP] Japan ................... 7-121665
Jul. 26, 1995 [JP] Japan ................... 7-190063

[51] Int. Cl.$^6$ .................................................. G01N 35/02
[52] U.S. Cl. .......................... 422/67; 422/64; 436/47; 436/49; 436/50; 436/150; 364/500
[58] Field of Search .................................... 422/63, 64, 67; 436/43, 47, 49, 50, 174, 180; 364/500

[56] References Cited

U.S. PATENT DOCUMENTS

| | | | |
|---|---|---|---|
| 4,313,735 | 2/1982 | Yamashita et al. | 422/67 |
| 4,457,893 | 7/1984 | Takekawa | 422/64 |
| 4,459,265 | 7/1984 | Berglund | 422/64 |
| 4,512,852 | 4/1985 | Tsuboshima et al. | 204/1 T |
| 4,908,186 | 3/1990 | Sakamaki | 422/64 |
| 4,908,320 | 3/1990 | Zakowski et al. | 436/45 |
| 5,037,612 | 8/1991 | Takahashi et al. | 422/64 |
| 5,104,808 | 4/1992 | Laska et al. | 436/48 |
| 5,192,505 | 3/1993 | Sakagami | 422/64 |

FOREIGN PATENT DOCUMENTS

| 56-30650 | 3/1981 | Japan . |
|---|---|---|
| 59-24380 | 6/1984 | Japan . |

*Primary Examiner*—Long V. Le
*Attorney, Agent, or Firm*—Fay, Sharpe, Beall, Fagan, Minnich & McKee

[57] ABSTRACT

Before analysis, the correspondence between the vessel positions and the reaction vessels held in the vessel positions respectively at the time of completion of all the operations of a turntable upon completion of the last analysis are stored in a computer in advance. When a start switch is turned on, a judgment is made as to whether the correspondences between the vessel positions and the reaction vessels coincide with those stored in the computer or not. In the case of coincidence, reaction vessels in vessel positions are regarded as having been already cleaned, so that these reaction vessels are subjected to blank measurement and sample addition in the case of optical measurement, whereas these reaction vessels are directly subjected to sample addition in the case of ISE measurement.

2 Claims, 5 Drawing Sheets

AUTOMATIC ANALYZER HAVING CUVETTE CLEANING CONTROL DEVICE

BACKGROUND OF THE INVENTION

The present invention relates to an automatic analyzer, and particularly to an automatic analyzer in which cleaning, sample addition, reagent addition and sample measurement are performed with respect to a plurality of reaction vessels.

There is a known automatic analyzer in which a row of reaction vessels arranged in the form of a loop are repeatedly rotated by a predetermined quantity covering a plurality of reaction vessels so that all the operations from the cleaning of the reaction vessels to the measurement of samples are efficiently carried out on the reaction vessels in the meantime. A typical example of such an automatic analyzer is disclosed in Japanese patent application laid-open No. 59-24380 and Japanese patent application publication No. 56-30650. According to the Japanese patent application laid-open No. 59-24380 and the Japanese patent application publication No. 56-30650, a turntable carrying a large number of reaction vessels circularly arranged thereon at equal intervals is rotated repeatedly by one turn plus one pitch (one reaction vessel's width) so that all the predetermined operations are performed during the repeated rotation. It is a matter of course that the same effect as described above can be obtained, for example, when the turntable is rotated repeatedly by one turn minus one pitch or, for example, by a half turn plus (or minus) one pitch.

In this type of automatic analyzer, it is required to shorten the measurement time, because shortening the measurement time is very important, for example, in the case of measurement of an emergency sample.

In the conventional method, all reaction vessels are cleaned during the rotation of the turntable regardless of information as to whether each reaction vessel has been already used or not yet. If the rotation of the turntable is continued by the conventional method in order to shorten the period from the request of measurement of a sample to the addition of the sample, the same amount of cleanser and the same amount of rinsing liquid as those used when measurement was performed for the same period are however consumed.

Moreover, when the operation of the automatic analyzer starts, however, a reaction vessel located in a cleaning position generally is first cleaned, and the sample distributing operation is not carried out before the reaction vessel which has been cleaned reaches a sample addition position. That is, reaction vessels initially located between the cleaning position and the sample addition position pass through the sample addition position without being subjected to sample addition even in the case where those reaction vessels have been already cleaned. Accordingly, the period in which a reaction vessel cleaned in a cleaning position reaches a sample adding position on the basis of the operation of the automatic analyzer is required as sample addition time, which adds to the total measurement time.

SUMMARY OF THE INVENTION

An object of the present invention is to provide an automatic analyzer suitable for shortening the measurement time.

Another object of the present invention is to provide an automatic analyzer suitable for shortening the time required up to the addition of the sample into the reaction and thus the total measurement time.

Still another object of the present invention is to provide an automatic analyzer in which only the used ones of all the reaction vessels are selectively cleaned to thereby shorten the time and reduce the amounts of cleanser and rinsing liquid consumed at the time of cleaning.

According to the present invention, an automatic analyzer is provided which comprises a turntable holding a plurality of reaction vessels, means for driving the turntable so that cleaning, sample addition, reagent addition and sample measurement are performed with respect to the plurality of reaction vessels, and means for judging whether the plurality of reaction vessels should be cleaned or not in advance of the sample addition so as to perform the cleaning with respect to those of the plurality of reaction vessels which should be cleaned and to prevent the remainder thereof from being cleaned.

According to another aspect of the present invention, an automatic analyzer is provided which comprises a turntable holding a plurality of reaction vessels, means for driving the turntable so that cleaning, sample addition, reagent addition and sample measurement are performed with respect to the plurality of reaction vessels, and means for judging whether those ones of the plurality of reaction vessels which are located between a cleaning position at which the cleaning is performed and a sample addition position at which the sample addition is performed should be cleaned or not in advance of the sample addition when the analyzer starts to operate so as to perform the cleaning with respect to those of the plurality of reaction vessels which should be cleaned and to prevent the remainder thereof from being cleaned.

According to an additional aspect of the present invention, an automatic analyzer is provided which comprises a turntable holding a plurality of reaction vessels, means for driving the turntable so that cleaning, blank measurement, sample addition, reagent addition and optical sample measurement are performed with respect to the plurality of vessels when the plurality of reaction vessels are located at corresponding positions thereto, and means for judging in advance of the sample addition whether those of the plurality of vessels which are located between the cleaning position and the sample addition position should be cleaned when the analyzer starts to operate so as to perform the cleaning with respect to those of the reaction vessels located between the cleaning position and the sample addition position which should be cleaned, and so as to prevent the remainder thereof from being cleaned to start the blank measurement from the remainder prevented from being cleaned.

According to yet another aspect of the present invention, an automatic analyzer is provided which comprises a turntable holding a plurality of reaction vessels, means for driving the turntable so that cleaning, sample addition, reagent addition and ion-selective electrode measurement are performed with respect to the plurality of vessels when the plurality of reaction vessels are located at corresponding positions thereto, and means for judging in advance of the sample addition whether those ones of the plurality of vessels which are located between the cleaning position and the sample addition position should be cleaned when the analyzer starts to operate so as to perform the cleaning with respect to those of the reaction vessels located between the cleaning position and the sample addition position which should be cleaned, and so as to prevent the remainder thereof from being cleaned to start the sample addition from the remainder prevented from being cleaned.

According to a further additional aspect of the present invention, an automatic analyzer is provided which comprises a turntable holding a plurality of reaction vessels, means for driving the turntable so that cleaning, blank measurement, sample addition, reagent addition and optical sample measurement are performed with respect to each of the plurality of reaction vessels, and means for judging whether each of the plurality of reaction vessels should be cleaned or not so as to perform the cleaning with respect to those ones of the plurality of reaction vessels which should be cleaned to perform the blank measurement with respect to the same, and so as to prevent the remainder of the plurality of reaction vessels from being cleaned to perform the blank measurement with respect to the same.

These and other objects and features of the present invention will become apparent from the descriptions of preferred embodiments of the present invention taken in connection with the accompanying drawings.

DESCRIPTION OF THE PREFERRED EMBODIMENTS

Figure 1:
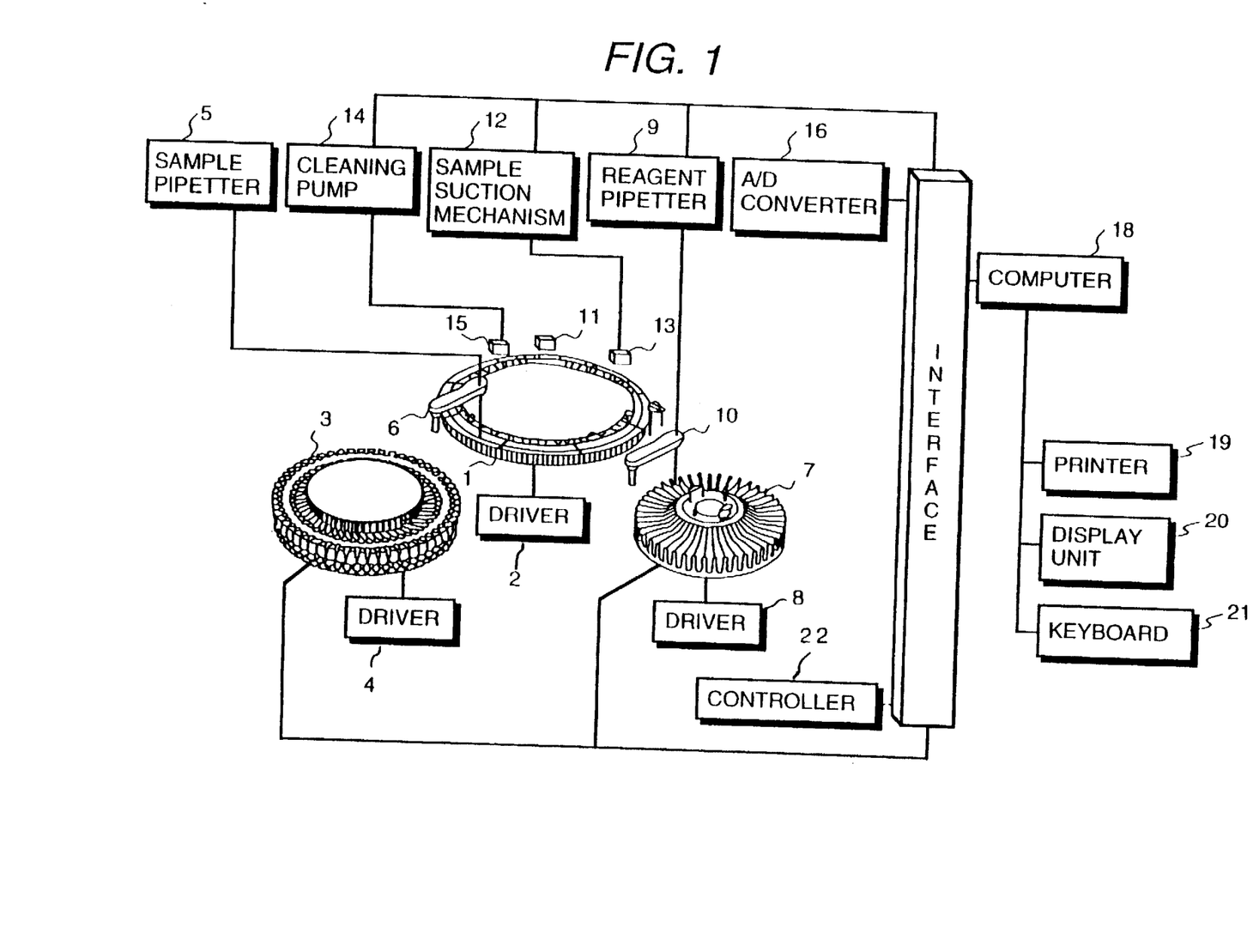
FIG. 1 is an overall configuration conceptual view of an automatic analyzer showing an embodiment of the present invention.

Referring to FIG. 1, a disc-like turntable 1 holds a large number of reaction cells or vessels so that these reaction vessels are arranged circularly at equal intervals. The turntable 1 is repeatedly rotated by a driver 2 intermittently by a predetermined quantity covering one turn plus one pitch (one reaction vessel's width). As a result, the turntable 1 advances by one pitch (one reaction vessel's width) each time the intermittent rotation is performed.

A sample disc 3 holds a large number of samples in a manner so that these samples are arranged circularly at equal intervals. The sample disc 3 is rotated by a driver 4 one pitch by one pitch (one sample's width). As a result, each sample on the sample disc 3 is added into each reaction vessel of the turntable 1 in the sample addition position by means of a sample pipetter 5 through a sample adder 6.

A reagent disc 7 holds a large number of reagents in a manner so that these reagents are arranged circularly at equal intervals. The reagent disc 7 is rotated by a driver 8. As a result, the reagent on the reagent disc 7 is distributed, that is, added into a sample-added reaction vessel of the turntable 1 in a reagent addition position by means of a reagent pipetter 9 through a reagent adder 10. The sample and reagent in the reaction vessel are stirred in a stirring position, so that they react with each other.

A liquid product of reaction between the sample and the reagent is subjected to absorbance measurement with respect to predetermined measurement items in an optical measurement position under a plurality of wave lengths by a photometer 11. Further, in the case where measurement using an ion-selective electrode (hereinafter simply referred to as ISE measurement) is required, a sample supplied with a reagent is sucked to an ion-selective electrode measurer 13 through a suction nozzle (not shown) by a sample suction mechanism 12 in a sample suction position for ISE measurement. Here, electromotive forces generated by the ion-selective electrode with respect to predetermined measurement items, for example, with respect to sodium, potassium and chlorine, are measured. Of course, this measurement is not carried out if the ISE measurement is needless. Incidentally, in the case of ISE measurement, the reagent is only used for diluting the sample.

A signal indicating absorbance is A/D-converted by an A/D converter 16 and then fetched into a computer 18 through an interface 17. A signal indicating electromotive force and obtained by ISE measurement is fetched into the computer 18 in the same manner as described above. The measurement results thus fetched into the computer 18 are printed out by a printer 19 and displayed on a display unit 20. On the display unit 20, measurement conditions, automatic analyzer running states, etc. are displayed as others. Through a keyboard 21, an operator can input information of measurement conditions, etc. while watching the display unit 20.

The reaction vessel of the completely measured sample is cleaned in a cleaning position by a cleaning pump 14 through a cleaning mechanism 15. Pure water is injected into the completely cleaned reaction vessel for the purpose of blank measurement. The injection of pure water may be carried out in a vessel position 2 (See FIG. 2) by the cleaning mechanism 15 or in a vessel position 3 or 4 (see FIG. 2) by a pure water injection mechanism (not shown) before the blank measurement. In either case, the blank measurement with respect to the reaction vessel supplied with the injected pure water is performed by the photometer 11 when the reaction vessel reaches a blank measurement position. That is, 100% adjustment in the base of transmittance (zero adjustment on the absorbance base) is performed. Incidentally, the 100% adjustment is required only in the case of optical measurement using the photometer 11, but it is not necessary to be carried out in the case of ISE measurement.

As described above, the turntable 1 rotates repeatedly intermittently by a quantity covering one turn plus one pitch whereas cleaning, sample addition, stirring and sample suction for ISE measurement are carried out in a stop period between the intermittent rotation periods of the turntable 1. Further, not only the optical measurement (absorbance measurement) of the liquid product of reaction is performed in the optical measurement position 13 (see FIG. 2) in the period in which the turntable 1 rotates, but also the blank measurement of the reaction vessel in the blank measurement position is performed in the same manner as described above in the period in which the turntable 1 rotates. On the other hand, the addition of the reagent is generally performed in the stop period between the intermittent rotation periods of the turntable 1, that is to say, in a temporary stop period provided in the middle of the intermittent rotation.

A controller 22 serves to control respective parts in accordance with a predetermined program on the basis of an instruction of the computer 18. That is, not only cleaning, 'blank measurement, sample addition and reagent addition are performed when these reaction vessels move to the cleaning position, the bank measurement position, the sample addition position and the reagent addition position respectively, but also the optical measurement and ISE measurement are performed in the optical measurement position and in the ISE measurement position respectively. The control on the respective parts to carry out such work in predetermined timing is performed by the controller 22.

Figure 2:
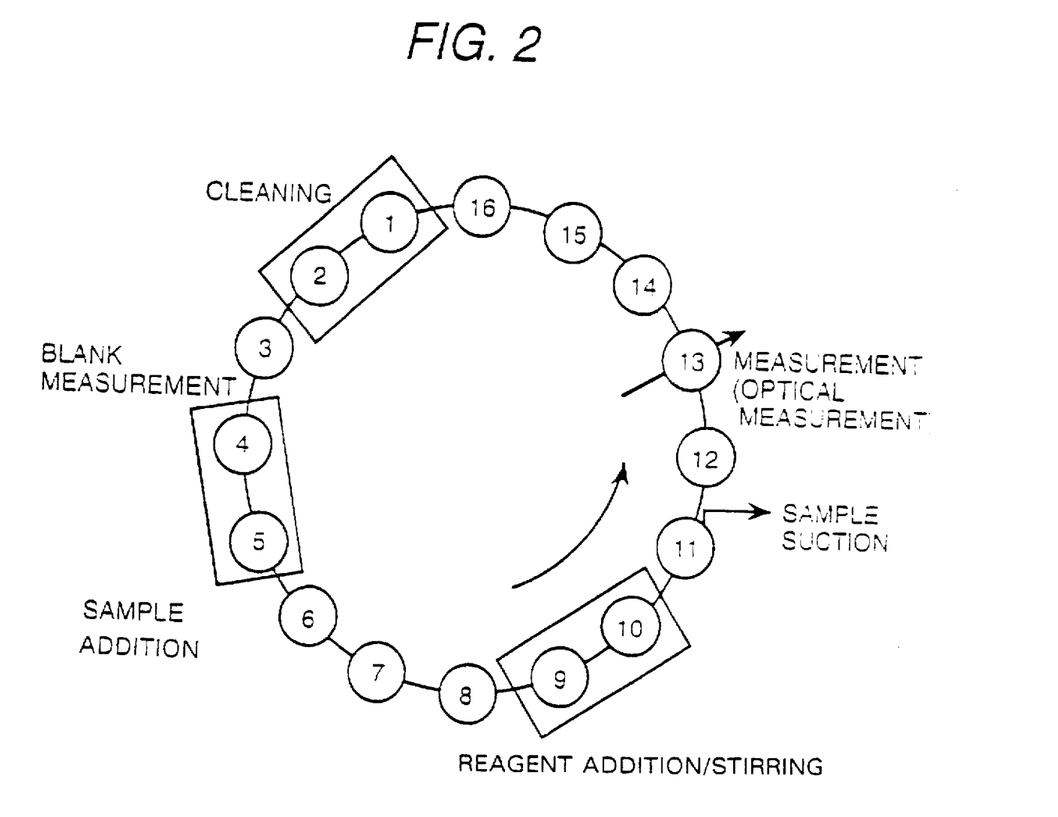
FIG. 2 is a view for explaining the relations between the rotating operation of a reaction table and respective work positions.

FIG. 2 shows the relation between the reaction vessel position and work position of the turntable 1. For simplification, FIG. 2 shows, by way of example, the case where 16 reaction vessels are used. In FIG. 2, the encircled reference numerals designate numbers indicating respective reaction vessel positions which are stationary or do not change even when the turntable 1 rotates.

The vessel positions 1 and 2 are cleaning positions. Cleaning is generally performed in the vessel positions 1 and 2 by using a period in which the turntable 1 stops whenever the reaction disc 1 rotates by the predetermined quantity (one turn plus one pitch). Accordingly, each reaction vessel is cleaned twice.

The vessel positions 4 and 5 are blank measurement positions. In a period in which the turntable 1 rotates by the predetermined quantity, a reaction vessel in the vessel position 4 is subjected to blank measurement by the photometer 11 and moves to the vessel position 5. When the reaction vessel reaches the vessel position 5, the reaction vessel is further subjected to blank measurement by the photometer 11 in a further turn by the predetermined quantity. That is, blank measurement of one reaction vessel is performed twice. Incidentally, measurement wavelengths in the first blank measurement and in the second blank measurement are set so as to be different from each other.

The vessel position 6 is a sample addition position. Here, sample addition is performed in a stop period in which the rotation of the turntable 1 stops each time the turntable 1 rotates by the predetermined quantity. The vessel position 9 is a reagent addition position. The addition of the reagent is generally performed in a temporary stop period provided in the middle of the period of the intermittent rotation by the predetermined quantity, rather than in a stop period between the intermittent rotation periods of the turntable 1. The vessel position 10 is a stirring position. The timing of stirring is the same as the timing of reagent addition.

The vessel position 11 is a sample suction position for ISE measurement. Sample suction for ISE measurement is carried out in the sample suction position by using the stop period in which the turntable 1 stops each time the turntable 1 is rotated by the predetermined quantity.

Optical measurement is performed in the vessel position 13 by the photometer 11 in the rotation period each time the turntable 1 rotates by the predetermined quantity.

Figure 3:
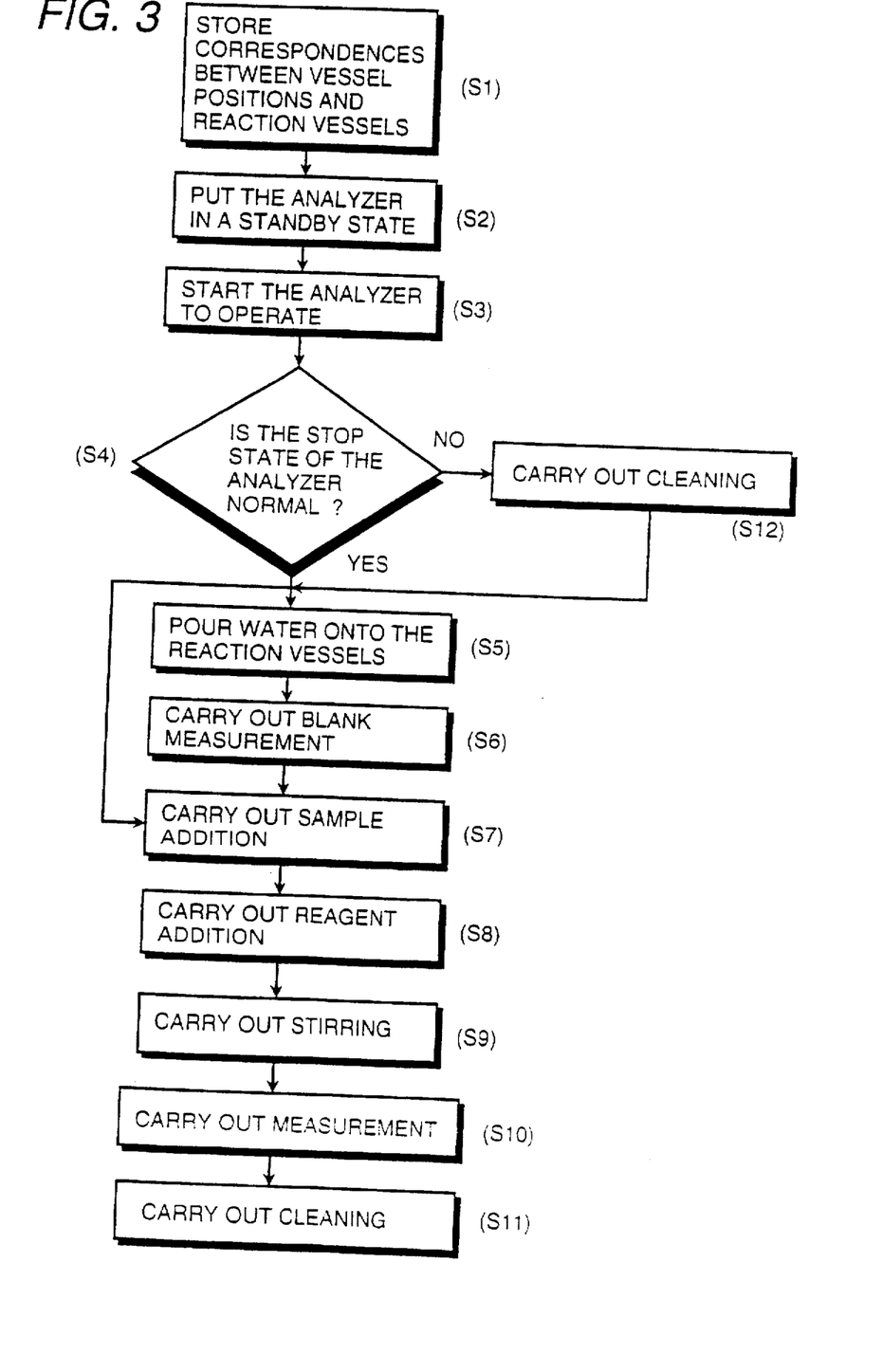
FIG. 3 is a flow chart showing an example of an operation of the automatic analyzer according to the present invention.

Referring to FIG. 3, the correspondences between the vessel positions 1 to 16 and the reaction vessels held in these vessel positions at the point of time when analysis is finished to complete all operations of the turntable 1, are stored in a storage device of the computer 18 in advance (S1). By the storage, preparation for the next analysis is completed (standby state) (S2). Incidentally, the vessel positions are generally numbered and the reaction vessels are generally numbered. Accordingly, the vessel positions and the reaction vessels in these vessel positions can be correlated with each other easily by such numbers.

When in the standby state, a start switch is turned on to start the operation of the analyzer (S3), a judgment is made as to whether the stop state of the analyzer is normal or not, that is, as to whether the correspondences between the vessel positions and the reaction vessels held in these vessel positions coincide with the correspondences stored (S4). In practice, it is sufficient if this judgment and the aforementioned storage are made with respect to the correspondences between the vessel positions from the cleaning position to the sample addition position 3 to 6 and the reaction vessels held in these vessel positions.

When the result of the judgment is Yes, this indicates that the reaction vessels in the vessel positions 3 to 6 have been already cleaned in the cleaning positions, that is, the reaction vessels need not be cleaned any more. Hence, these reaction vessels are subjected to pure water injection (S5), blank measurement (S6) and sample addition (S7) in the case of optical measurement (colorimetry) whereas these reaction vessels are directly subjected to sample addition (S7)in the case of ISE measurement.

After the sample addition, reagent addition (S8), stirring (S9) and then optical measurement (S10), that is, absorbency measurement, are performed in the case of optical measurement, whereas reagent addition (S8), stirring (S9) and the sample suction for ISE measurement are performed in the case of ISE measurement. Of course, the sucked sample is subjected to ISE measurement (S10). After completion of the measurement, cleaning (S11) is performed.

There may be the possibility that the correspondences between the vessel positions and the reaction vessels held in these vessel positions are not coincident with the stored correspondences by some cause. As an extraordinary case, for example, there is the case where the reaction vessels are replaced by new ones after completion of all the operations of the analyzer. In such a case, the judgment in the step S4 results in No, so that the reaction vessels are cleaned in the vessel positions 1 and 2 successively (S12) when the reaction vessels passes through the vessel positions 1 and 2. Further, in the case of optical measurement (absorbance measurement), the reaction vessel in the vessel position 1 is subjected to blank measurement in the vessel positions 4 and 5 after injection of pure water, and then a sample is distributed into the reaction vessel when the reaction vessel reaches the vessel position 6. On the other hand, in the case of ISE measurement, unless the reaction vessel in the vessel position 1 reaches the vessel position 6, the sample is not added into the reaction vessel.

Incidentally, blank measurement, sample addition, reagent addition, stirring, sample suction for ISE measurement, optical measurement and cleaning are specifically quite equivalent to those explained above with reference to FIGS. 1 and 2.

Assuming now that the time required for the intermittent rotation of the turntable 1 by the predetermined quantity (one turn plus one pitch) is 18 sec., then the time from the start of the operation of the analyzer to the sample addition is constantly 5×18=90 sec. in the conventional example, whereas the time in ISE measurement is 0 sec. and the time in optical measurement (absorbency measurement) is 2×18= 36 sec. in the case where the judgment in the step S4 in this embodiment of the present invention results in Yes. Accordingly, it is apparent that the time up to the sample addition in the embodiment of the present invention is shortened extremely compared with that in the conventional example. This obviously arrives at a conclusion that the total measurement time is shortened.

It is apparent from the above description that, according to the present invention, there is provided an automatic analyzer which is suitable for shortening the time required for adding a sample into a reaction vessel, that is, shortening the total measurement time.

Figure 4:
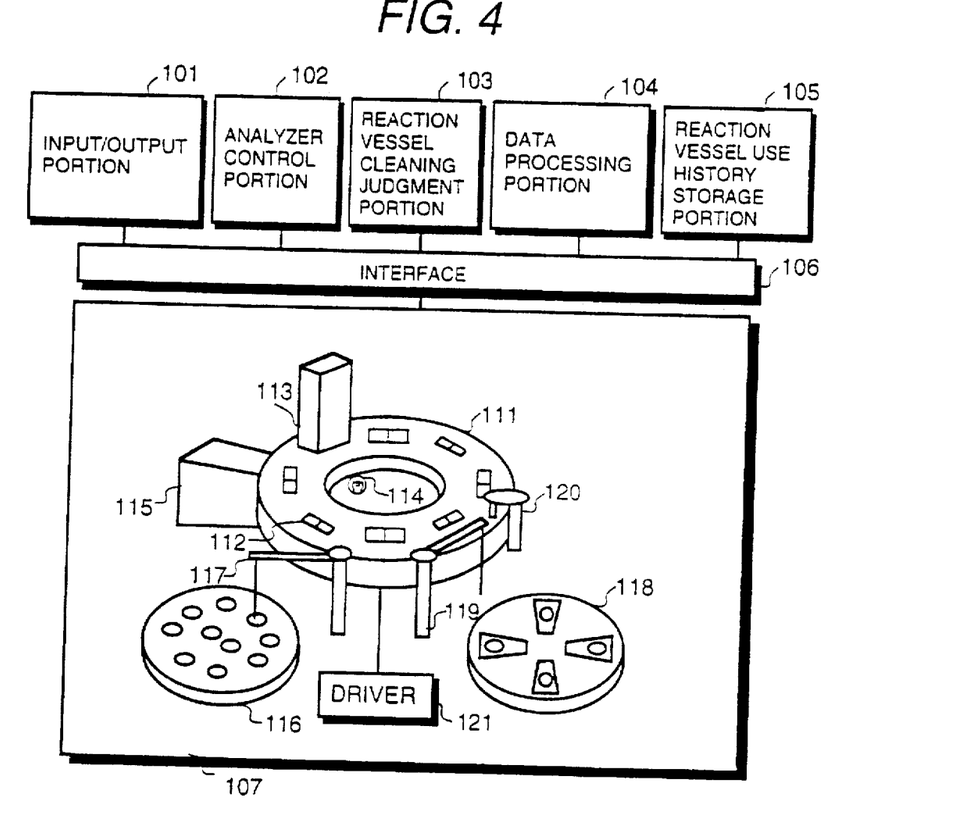
FIG. 4 is an overall configuration view showing another embodiment of the automatic analyzer according to the present invention.

Referring to FIG. 4, an embodiment of an automatic analyzer shown in FIG. 4 comprises an input/output portion 101, an analyzer control portion 102, a reaction vessel cleaning judgment portion 103, a data processing portion 104, a reaction vessel use history storage portion 105, an analysis portion 107, and an interface 6 for connecting those portions.

A disk-like turntable 111 is designed to be rotatable by a driver 121 while it carries, on its circumference, reaction cells or vessels 112 which are n in number. When an instruction to start measurement is given from the input/output portion 101, a resetting operation is carried out so that first any reaction vessel 112 to be used is brought into a start position. Then, the turntable 111 starts its rotation, so that first, the reaction vessel 112 moves to a reaction vessel cleaning portion 113 so as to be cleaned by use of a cleanser or a rinsing liquid.

Succeedingly, a blank specimen (deionized water) is injected into the reaction vessel 112 by the reaction vessel cleaning portion 113 through a blank specimen discharge portion incorporated in the reaction vessel cleaning portion 113, so that optical measurement is performed when the reaction vessel 112 passes on an optical axis connecting a light source 114 to a spectrophotometer 115. The measured value which is a blank value having information, such as the damage and stain of the vessel at the time of measurement, the drifting of brightness of a lamp and the change of the characteristic of an electric circuit, is stored in the data processing portion so as to be used for zero adjustment of the value of optical measurement, which will be measured in the later step, of a specimen obtained by reaction of a sample with a reagent. Thereafter, optical measurement for zero adjustment is referred to as "blank measurement". Succeedingly, the reaction vessel 112 is dried at the reaction vessel cleaning portion 113 and then reaches a sample addition position . Here, a sample on a sample disc 16 is added to the reaction vessel 112 by means of a sample addition mechanism 117.

Further succeedingly, the reaction vessel 112 reaches a reagent addition position, so that a reagent on the reagent disc 118 is supplied into the reaction vessel 112 by means of a reagent addition mechanism 119 and the sample and the reagent in the reaction vessel 112 are stirred by means of a stirring mechanism 120. The turntable 111 further continues its rotation so that the reaction vessels 12 on the turntable 11 pass through the optical axis connecting the light source 114 and the spectrometer 115 at time intervals of about 18 sec. The spectrometer 115 performs optical measurement of the specimen in the reaction vessel 112 which passes through this optical axis. The measured values of the spectrometer 115 are fed to the data processing portion 104. When the optically measured data are collected, the data processing portion 104 corrects the optically measured data of the specimen on the basis of the blank value, converts the corrected value into a value of, for example, the concentration of a matter contained in the sample, and outputs the thus obtained value through the input/output portion 101. In parallel with this processing operation, the turntable 111 further continues its rotation, so that the reaction vessel 112 reaches the reaction vessel cleaning portion 113 so as to be cleaned with a cleanser or a rinsing liquid again. Thereafter, the measurement of the blank value is performed so as to be used for measurement again.

Figure 5:
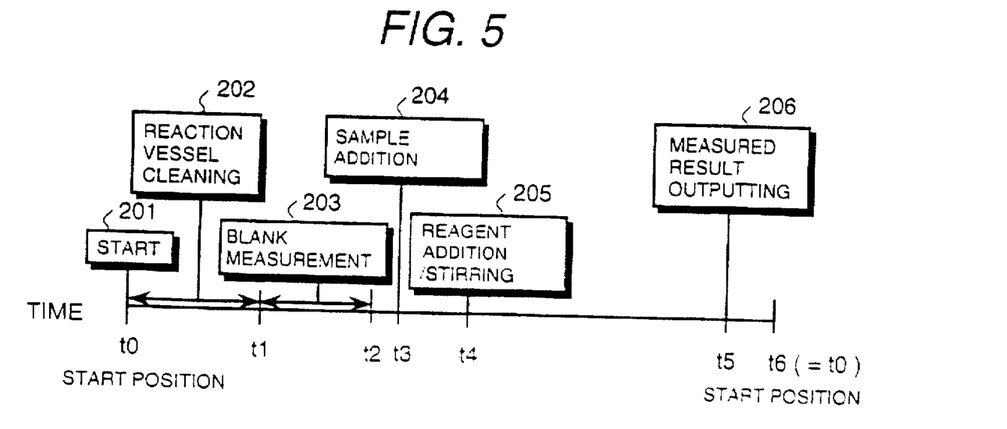
FIG. 5 is a detailed time chart with respect to one of the reaction vessels.

The aforementioned operation carried out on the reaction vessel 112 can be summarized as shown in FIG. 5. When a head reaction vessel located in a start position starts at time t0 (201), the cleaning of the head reaction cell is completed at time t1 (202), the blank measurement is completed at time t2 (203), the sample addition is performed at time t3 (204), the reagent addition/stirring is performed at time t4 (205), the measured result is output at time t5 (206) and the head reaction vessel goes back to the start position again at time t6. If the analyzer control portion 102 gives an instruction to continue the operation with no change, the same operation as that in a period from time t0 to time t6 is repeated from time t6 as a start point.

Figure 6:
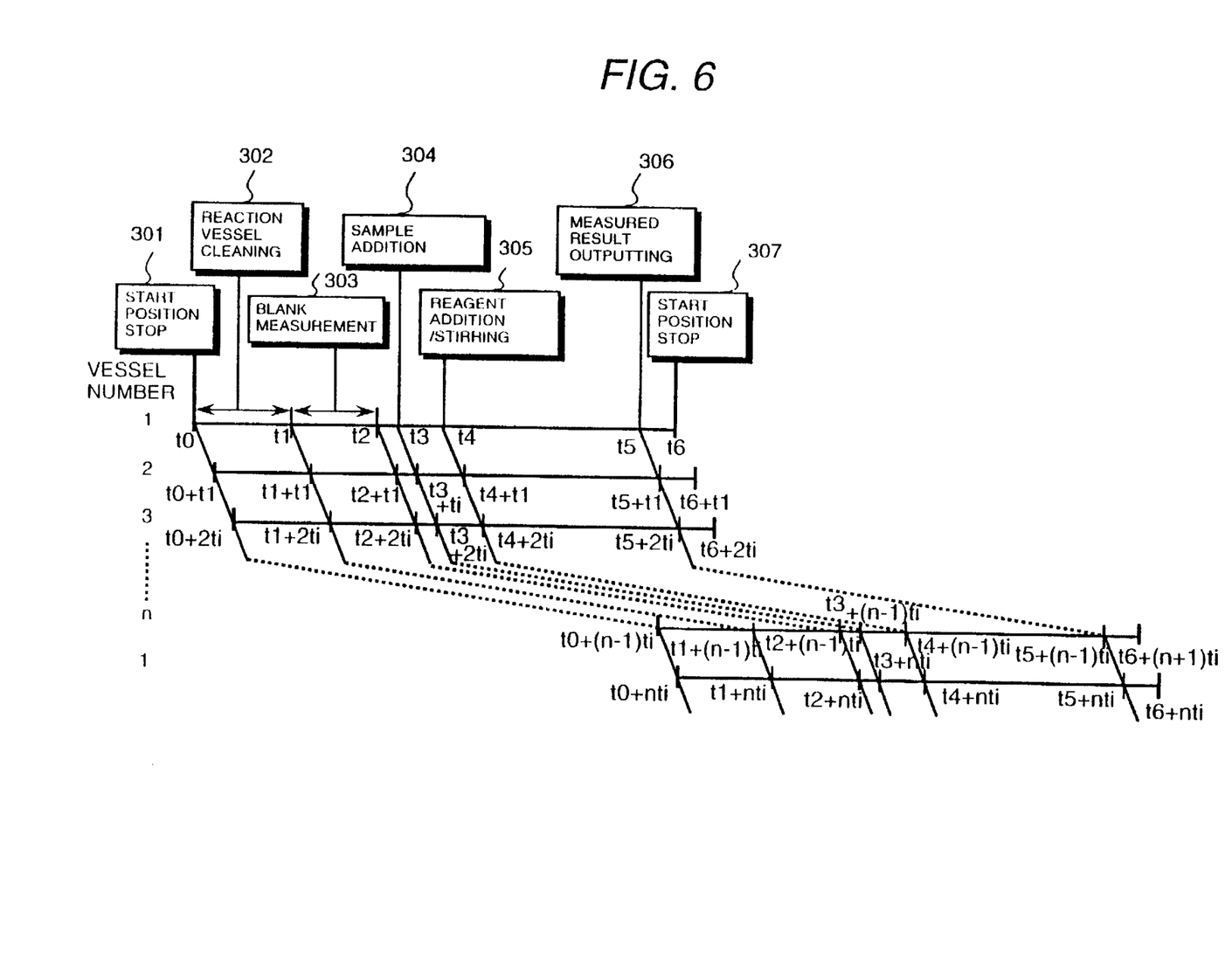
FIG. 6 is a time chart with respect to all the reaction vessels.

In the automatic analyzer of this embodiment, reaction vessels which are n in number are used so that the reaction vessels come to the start position successively one after one at time intervals of ti=(t6-t0)/n. This can be carried out by repeatedly rotating intermittently the turntable 111 by a predetermined quantity covering one turn plus one pitch (one reaction vessel's width) as in the embodiment explained in connection with FIGS. 1 to 3. When attention is put on the whole of the reaction vessels, the time schedule of operations carried out on the reaction vessels is as shown in FIG. 6. Each of the respective reaction vessels gets in the states of start position stop 301, reaction cell cleaning 302, blank measurement 303, sample addition 304, reagent addition/stirring 305 and measured result output 306 successively one after one at intervals of time ti. That is, so long as the turntable 111 continues its rotation, the blank measurement can be started on any one of the reaction vessels within time ti.

Incidentally, the automatic analyzer of this embodiment is designed so that the input/output portion 101 can switch the mode of measurement between an emergency sample measurement mode and an ordinary sample measurement mode.

In the ordinary sample measurement mode, the operation of the analysis portion stops at the point of time when the cleaning of the finally used reaction vessel is completed. During the stop of the operation, there is no consumption of the reaction cell cleanser or rinsing liquid. When measurement is started from the state in which the analysis portion stops, however, the reaction vessels must be always cleaned in the order starting from the head reaction vessel before sample addition is started. Accordingly, time t3-t0 is required.

On the other hand, in the emergency sample measurement mode, the operation of the turntable 111 is continued, regardless of the presence of the measurement instruction from the input/output portion 101, until the emergency sample measurement mode is canceled after the mode is once set. In the period of the continuous operation, the reaction vessel cleaning judgment portion 103 judges, on the basis of information in the reaction cell use history storage portion 105, whether the reaction vessel 112 requires cleaning or not.

Information as to whether or not the reaction vessel is used after the cleaning in the last routine is stored in the reaction vessel use history storage portion 105. When the reaction vessel is supplied with a sample or reagent to be used as a reaction vessel after the cleaning of the reaction vessel in the last time, when the sample in the reaction vessel is diluted after that, or when the reaction vessel is filled with a cleanser, instead of a reagent, for the purpose of cleaning, the reaction vessel cleaning judgment portion 103 makes a decision that the reaction vessel requires cleaning.

Further, information as to whether or not each reaction vessel has been cleaned one or more times after the emergency sample measurement mode is selected is stored in the reaction vessel use history storage portion 105. When no cleaning has been performed, the reaction vessel cleaning judgment portion 103 makes a decision that the reaction vessel requires cleaning.

Further, with respect to a reaction vessel which has been cleaned lastly, information as to the time passed from the cleaning (this time can be judged from the machine cycles which have passed) is stored in the reaction vessel use history storage portion 105. When the time exceeds the time-out period designated separately or input from the input/output portion 1, the reaction vessel cleaning judgment portion 103 makes a decision that the reaction vessel requires cleaning.

When all the conditions mentioned above are not applied to a certain reaction vessel, that is, when a certain reaction vessel does not require cleaning, the reaction vessel cleaning judgment portion 103 makes a decision that the reaction vessel does not require cleaning. On the basis of the result of judgment, the analyzer control portion 102 gives an instruction to the reaction vessel cleaning mechanism 113 so as to perform or not to perform reaction vessel cleaning 302 so that the reaction vessel cleaning mechanism 113 selectively cleans only the reaction vessels 12 to which the cleaning instruction is given. If control is made so that all the reaction vessels before the blank measurement have been cleaned in such a manner as described above, the blank measurement can be performed within time ti. Accordingly, even in the case where emergency measurement is requested, the blank measurement can be performed and sample addition can be started within time t3−t1+ti.

The required period of time from the request of measurement to the start of the sample addition operation is compared between the ordinary sample measurement mode and the emergency sample measurement mode. It is now assumed that the automatic analyzer of this embodiment can make measurement 800 times per hour. It is further assumed that respective times in the automatic analyzer are as follows: t0=0 sec., t1=63 sec., t2=117 sec., t3=121.5 sec. and ti=4.5 sec. In the ordinary sample measurement mode, the sample addition starts within the time t3−t0=121.5 sec. In the emergency sample measurement mode, the sample addition starts within the time t3−t1+ti=63 sec. That is, in the emergency sample measurement mode, analysis can be started within about half the time required in the ordinary sample measurement mode.

Assuming now that 125 microliters of cleanser and 1800 microliters of rinsing liquid are consumed for every reaction vessel cleaning in the automatic analyzer of this embodiment, and that all of the reaction vessels 12 are cleaned in the condition in which the automatic analyzer is operated for 24 hours in the emergency sample standby mode, then cleaning must be required by 19200 times. The amount of cleanser and the amount of rinsing liquid consumed for the 24 hours are 2.4 liters and 34.6 liters respectively.

On the contrary, assuming that only the reaction vessels which should be cleaned are cleaned selectively and that the number of times of analyzing is m, the consumed amounts of cleanser and rinsing liquid can be reduced to (125×m) microliters and (180×m) microliters respectively. Further, even in the case where the judgment logic in the reaction vessel cleaning judgment portion is set so that the reaction vessels are always cleaned at the time of initial reaction cell cleaning after the setting of the emergency sample measurement mode, the consumed amounts of cleanser and rinsing liquid can be reduced to (125×(m+n)) microliters and (1800×(m+n)) microliters, respectively.

It is to be understood from the above description that the number of times of the cleaning of reaction vessels in the automatic analyzer can be reduced to the required minimum so that reduction of the consumed amounts of cleanser and rinsing liquid and reduction of time can be attained.

Since it is obvious that many changes and modifications can be made in the above described details without departing from the nature and spirit of the present invention, it is to be understood that the present invention is not to be limited to the details described herein.

What is claimed is:

1. An automatic analyzer, comprising:

a turntable holding a plurality of reaction vessels;

means for driving the turntable so that cleaning, blank measurement, sample addition, reagent addition, and optical sample measurement are performed with respect to the plurality of reaction vessels when the plurality of reaction vessels are located at positions corresponding to the cleaning, the blank measurement, the sample addition, the reagent addition, and the optical sample measurement;

means for judging in advance of the sample addition whether any of said plurality of reaction vessels which are located between the cleaning position and the sample addition position should be cleaned when the analyzer starts to operate so as to perform the cleaning with respect to at least one of the reaction vessels located between the cleaning position and the sample addition position which should be cleaned, and so as to prevent the remainder thereof from being cleaned to start the blank measurement from the remainder prevented from being cleaned; and means for storing correspondences between the plurality of reaction vessels and vessel positions at which the plurality of reaction vessels are held by the turntable, the correspondences being those after the turntable finishes operating;

wherein the judging means judges whether the reaction vessels which are located between the cleaning position and the sample addition position should be cleaned or not based on the stored correspondences.

2. An automatic analyzer, comprising:

a turntable holding a plurality of reaction vessels;

means for driving the turntable so that cleaning, sample addition, reagent addition, and ion-selective electrode measurement are performed with respect to the plurality of reaction vessels when the plurality of reaction vessels are located at corresponding positions to the cleaning, the sample addition, the reagent addition, and the ion-selective electrode measurement;

means for judging in advance of the sample addition whether any of the plurality of reaction vessels which are located between the cleaning position and the sample addition position should be cleaned when the analyzer starts to operate so as to perform the cleaning with respect to at least one of the reaction vessels located between the cleaning position and the sample addition position which should be cleaned, and so as to prevent the remainder thereof from being cleaned to start the sample addition from the remainder prevented from being cleaned; and means for storing correspondences between the plurality of reaction vessels and vessel positions at which the plurality of reaction vessels are held by the turntable, the correspondences being those after the turntable finishes operating;

wherein the judging means judges whether the reaction vessels which are located between the cleaning position and the sample addition position should be cleaned or not based on the stored correspondences.

* * * * *